United States Patent [19]

Ranalletta et al.

[11] Patent Number: 4,892,097

[45] Date of Patent: Jan. 9, 1990

[54] RETRACTABLE FINGER LANCET

[75] Inventors: Joseph V. Ranalletta; Rowland W. Kanner, both of Guntersville, Ala.

[73] Assignee: Ryder International Corporation, Arab, Ala.

[21] Appl. No.: 153,968

[22] Filed: Feb. 9, 1988

[51] Int. Cl.$^4$ ............................................... A61B 17/32
[52] U.S. Cl. .................................... 606/182; 128/329 R
[58] Field of Search .................. 128/314, 315, 329 R, 128/770; 604/136, 157

[56] References Cited

U.S. PATENT DOCUMENTS

| | | | |
|---|---|---|---|
| 3,903,887 | 9/1975 | Antoshkiw | 128/221 |
| 4,078,552 | 3/1978 | Chen et al. | 128/2 G |
| 4,139,011 | 2/1979 | Benoit et al. | 128/329 |
| 4,358,539 | 11/1982 | Bittings | 435/301 |
| 4,379,456 | 4/1983 | Cornell et al. | 128/314 |
| 4,414,975 | 11/1983 | Ryder et al. | 128/314 |
| 4,455,510 | 5/1984 | Rigby | 128/329 |
| 4,539,988 | 9/1985 | Shirley et al. | 128/314 |
| 4,735,203 | 4/1988 | Ryder et al. | 128/314 |

Primary Examiner—Michael H. Thaler
Assistant Examiner—William Lewis
Attorney, Agent, or Firm—R. A. Giangiorgi, Trexler, Bushnell, Giangiorgi & Blackstone, Ltd.

[57] ABSTRACT

A two-piece, single-use, disposable lancet assembly includes a housing containing a lancet formed from a spring wire integrally formed with a sharpened, skin-piercing probe end section. The spring lancet is mounted within the housing and is secured in a retracted, pre-tensioned or cocked position. A lever-like bar hingedly secured to the housing serves both as a closure for the access opening in the housing and as a lever for dislodging and for releasing the tensioned spring wire to actuate the skin-piercing probe to pulse functionally through a base port in the housing and then automatically to retract irretrievably into the housing.

9 Claims, 2 Drawing Sheets

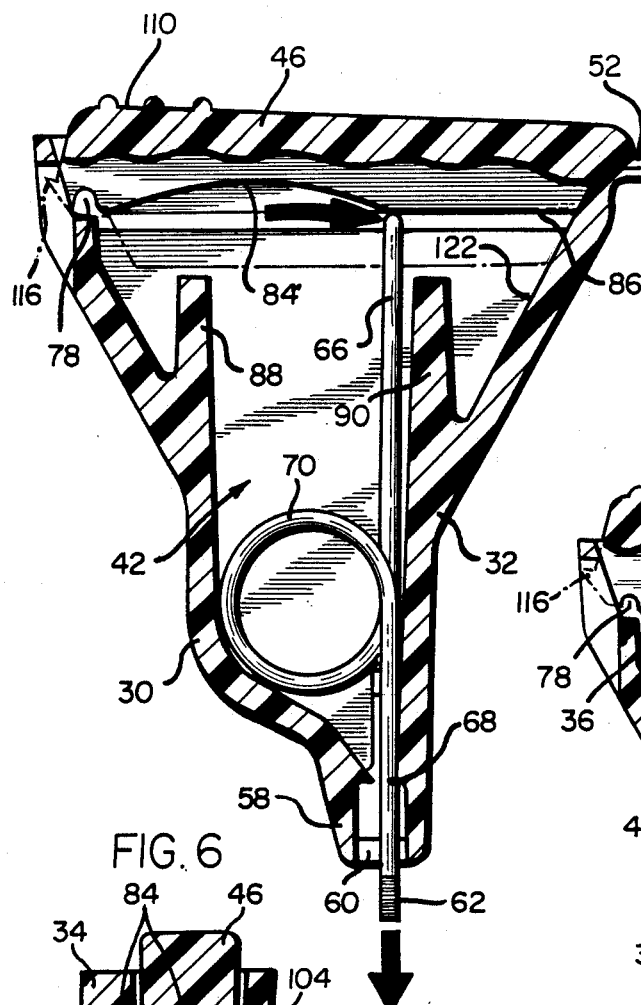
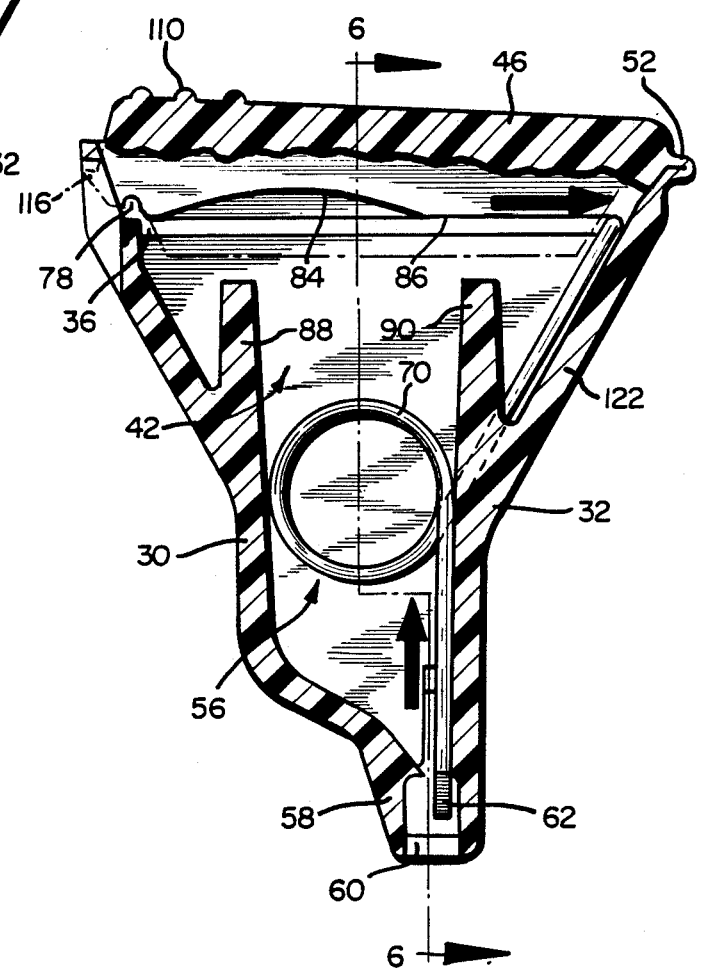
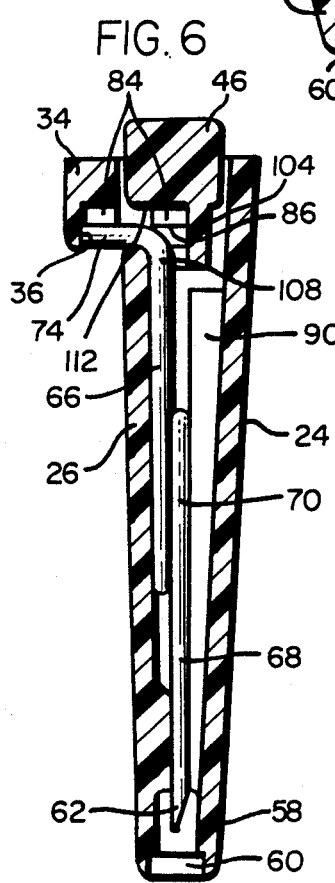
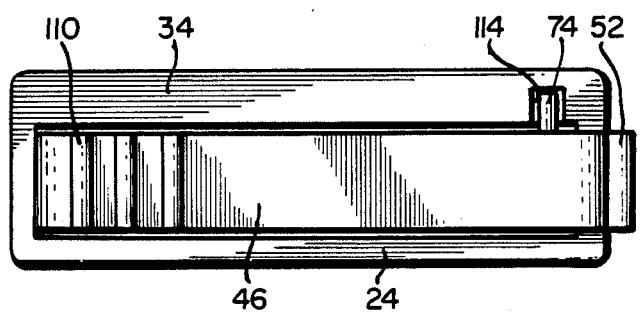

RETRACTABLE FINGER LANCET

FIELD OF THE INVENTION

The present invention relates to a retractable finger lancet assembly including a lancet for penetrating the skin of a patient to obtain blood samples for medical examination and testing. More particularly, the invention is directed to a lancet, a housing in which the lancet is stored and restrained in a tensioned configuration, and from which the lancet may be functionally projected, and including a mechanism by which the probe of the lancet is promptly and automatically retracted into the protective housing.

BACKGROUND OF THE INVENTION

Spring-energized or driven lancets of many and varied structual arrangements have been employed extensively to replace needles and hand-carried needle-like probes for piercing the skin, particularly the finger, to provide blood samples for examination and clinical testing. While these "automated" lancets have provided some inprovement and an enhanced degree of control in the procedures involved, the mechanisms themselves have disadvantages and objectionable features.

The relative complexity of some devices has contributed to these difficulties and has made the devices expensive in manufacture as well as unreliable in use. Excessive numbers of springs, plunger elements and other interrelated operating components have rendered many of the automated lancet assembles unduly complex. Others of prior art lancets are foreboding in their visual appearance and give rise to undue concern on the part of the patient.

It is, accordingly, a principal aim of the present invention to provide an automatic lancet having minimum physical components, and which is relatively simple in construction, uninhibiting in appearance, and which exhibits an enhanced simplicity and is reliable in use. The lancet of the present invention obviates many of the shortcomings and objectionable features of prior art devices.

SUMMARY OF THE INVENTION

The retractable finger lancet of the present invention is advantageously characterized in that it is exceedingly simple in construction. The lancet assembly consists of only two physical components—a housing of plastic composition and a spring having a sharpened end portion which constitutes the needle-like probe of the lancet.

It is a feature of the retractable finger lancet assembly of the invention that it includes an actuating spring which is secured and restrained within the housing in a pretensioned, cocked configuration, with the skin-piercing probe retracted so that it is protected and out of sight.

Another feature of the invention is that the housing is formed with a top access opening and that a lever-like bar is hingedly attached to the housing as a pivotally positionable closure therefor.

It is a related feature of the invention that digital pressure applied to the housing closure bar when the latter is in a housing-closing attitude is effective further to depress the bar and to release and to actuate the lancet spring, thereby causing the spring forcibly to elongate and project and to present its sharpened probe end functionally through a port formed in a base of the housing.

It is a further feature of the invention that upon actuation of the pretensioned and secured lancet spring by digitally effected dislodging displacement, the spring itself automatically traverses a series of uninterrupted sequential movements in which a skin-piercing end of the spring is extended to project, through a port, out from the housing and, thereupon, is promptly retracted into the housing to assume a withdrawn, inoperative and sequestered disposition.

A related feature of the invention is that the housing of the assembly is formed interiorly thereof with spaced guide walls delineating a path of travel of a central coiled body portion of the spring during execution of the sequence of movement thereof initiated upon release of the spring from its initial, retracted, pretensioned mode.

Yet another feature of the retractable lancet of the invention is a locking notch formed in a sidewall of the housing for releasably securing an end arm of the lancet spring there within to restrain the spring in a pretensioned, protected, stand-by mode.

A related feature of the invention is the provision in a sidewall of the assembly housing of a transverse, generally horizontal slot communicating with the spring arm locking notch, the slot defining a path of lateral travel of the spring arm therewithin when the latter is forcibly dislodged an released from the locking notch. Upon its release from the locked position, the spring arm snaps to travel across the lateral expanse of the housing and to effect concurrent lineal reciprocal movement of a probe end of the lancet spring downwardly and outwardly of the housing. Finally, without any interruption in the motion of the spring assembly, the probe end is automatically retracted inwardly into the housing.

Yet another feature of the invention is that an upper edge of the sidewall bounding the slot formed in the housing is vaulted upwardly to define a controlled, arcuate guide path to be traversed by the spring arm as the latter bears there against in its travel across the housing.

Another feature of the invention is the provision of cooperating interlocking elements at a free end of the lever-like, housing-closing bar and at a corresponding upper edge of the housing for retaining the closing bar in a position to overlie and to close a top opening in the housing.

Still another feature of the invention is that the spring lancet uses only a single spring element. The spring comprises a wire having a circularly looped or coiled center sector unitary with a pair of arms extending in a wing-like attitude from the center sector and tangentially thereof.

It is a structual feature of the lancet assembly of the invention that the housing is generally triangular or funnel shaped as viewed in front elevation, with a wide upwardly-opening upper section tapering to a narrow base formed with a restricted orifice through which the probe end of the lancet is forcibly projected during functional operation of the lancet. The probe end then automatically retracts to within the body of the housing.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings in which like reference numerals identify like elements, and in which:

FIG. 4 is a further cross-sectional view similar to FIGS. 2 and 3, and representing an intermediate stage of orientation of the spring wire lancet of the invention, the latter being shown in a partially tensioned mode, and the probe end of the lancet in a fully-extended, functional position, and with broken lines depicting a pivotally hinged cover of the housing in an open position;

FIG. 5 is a cross-sectional view similar to that shown in FIG. 4 and showing the spring lancet in a final and essentially untensioned and relaxed, after-use mode, with the probe end irretrievably retracted into the lancet housing;

FIG. 6 is a cross-sectional view taken substantially on the line 6—6 of FIG. 5; and FIG. 7 is a top plan view of the lancet assembly of the invention, with the spring lancet in an end position.

DETAILED DESCRIPTION OF ILLUSTRATED EMBODIMENT

Figure 1:
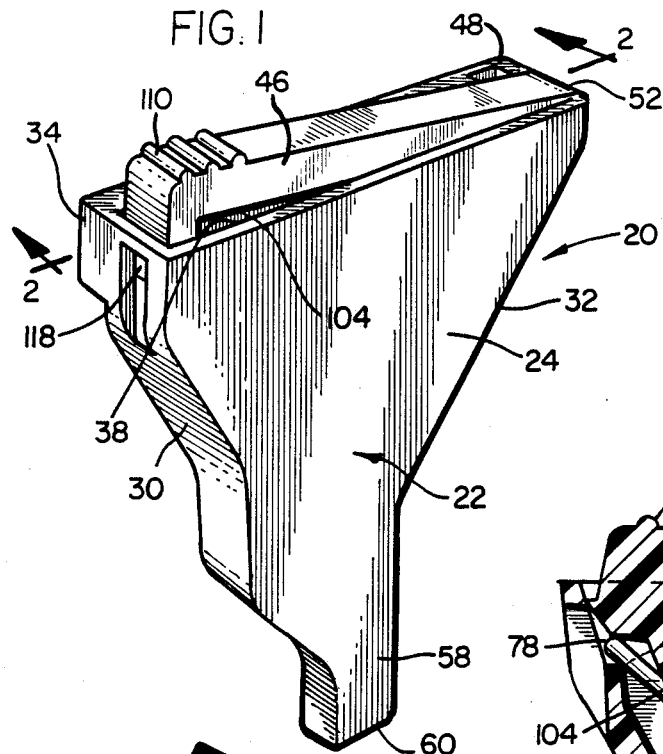
FIG. 1 is a perspective view of a retractable lancet assembly and illustrates a preferred embodiment of the device of the invention with the functional probe in a retracted position, as the assembly may appear before use.

The aims and objects of the invention are accomplished by providing in a retractable lancet assembly a simplified mechanical structure with a reduced number of functional physical components. The illustrated embodiment of the invention includes a plastic housing of unitary construction in combination with a wire spring element, the latter serving both as the lancing probe and as the means for functionally driving the skin-piercing probe. The spring utilized is preferably in the form of a resilient stainless steel wire having straight end sections projecting in generally opposed directions from a looped or coiled central body. The housing is formed internally with spring guide walls and with a spring securement notch in which an upper end portion of the spring is retained to restrain and hold the spring in a pretensioned mode. A digitally depressible lever integrally formed with the housing serves also as a bar for displacing the secured end of the tensioned spring to release the spring to permit the latter to pulse, causing its probe end to extend through a base orifice in the housing and then automatically to retract to a relaxed and spent mode, interiorly of the housing.

Referring now to the drawings, in a preferred embodiment of the retractable lancet of the invention, shown for illustrative purposes only and not to be construed in any limiting sense, the lancet assembly 20 is depicted (FIG. 1) as including hollow housing 22 of plastic material and having a generally funnel shaped configuration. The housing 22 includes spaced front and rear walls 24 and 26 joined by side walls 30 and 32. The housing 22 is illustratively shown as integrally molded in a unitary form corresponding generally to its final physical configuration. Alternatively, the housing may be molded in a spread or "opened" attitude in which the opposed side walls are initially disposed as opposed pages of an open book, and joined at inner edges thereof along a connecting live hinge, the latter being integrally formed with the sides of the housing, during the molding process.

As shown, the rear wall 26 of the lancet assembly includes at its upper end a rearwardly displaced, laterally extending section 34 (FIGS. 1 and 6) and with an elongate slot 36 extending transversly through the rear wall 26 along substantially a full lateral expanse thereof.

As indicated in FIG. 1, the housing 22 is formed with an upwardly directed top opening 38 providing access into the body cavity 42 or interior of the housing 22. A pivotally manipulatable lever-like bar 46 is hingedly fastened to the housing 22 at an upper end edge 48 thereof by means of a integrally formed web or live hinge 52. The bar 46 serves the dual function of a closure for the top opening 38 in the housing 22 and as an actuator for releasing a tensioned lancet spring 56 mounted within the cavity 42 of the housing 22 (FIGS. 2 through 6). At its lower end 58 the housing 22 is formed with a port or aperture 60 through which a lower or distal, sharpened skin-piercing terminal or probe end 62 of the spring 56 is directed forcibly to pulse and to project, and then automatically to retract during the use cycle of the lancet of the invention.

Figure 2:
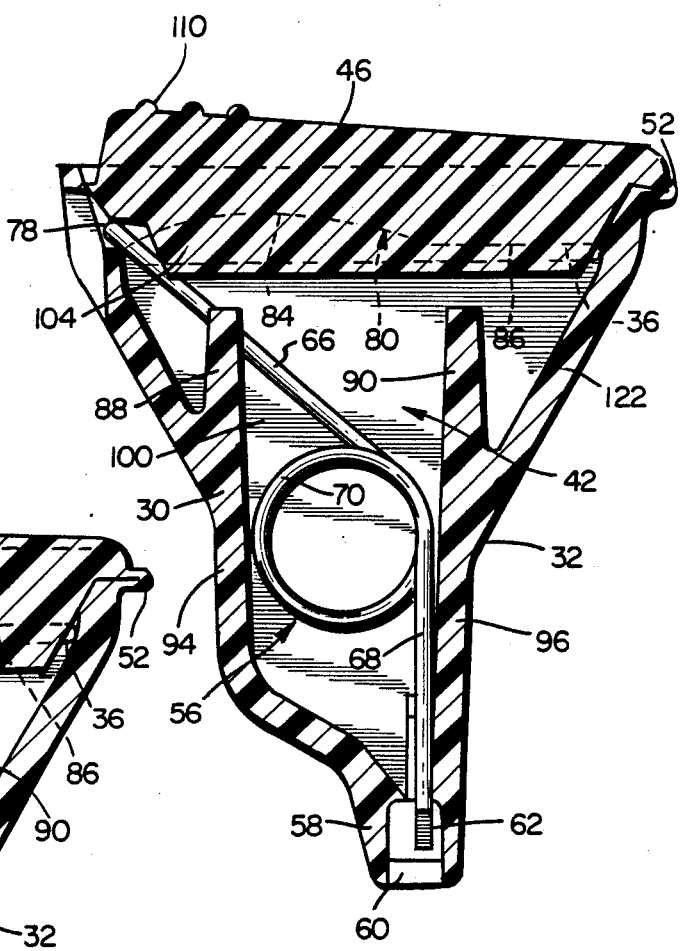
FIG. 2 is a cross-sectional view taken substantially on the line 2—2 of FIG. 1 and showing a spring wire probe releasably secured in a retracted, tensioned mode, within the housing.

FIGS. 2-6 show in somewhat greater detail additional structual features of the automatically retractable lancet assembly 20 of the invention and depict the successive orientations assumed by the lancet spring 56 during sequential operational modes of the assembly 20. In the illustrated embodiment of the invention, as best shown in FIG. 2, the lancet spring 56 is a wire having lineal, generally upwardly extending and downwardly extending opposed end sections 66 and 68 which are joined to, extend taugentially from and which are integrally formed with an immediately positioned looped or coiled section 70. The downwardly directed lower section 68 of the spring 56 terminates in the sharpened, skin piercing probe end 62. The upper lineal section 66 of the spring 56 is bent to provide an arm 74 (FIG. 6) extending normally of a plane defined by the looped spring section 70.

The arm 74 of the spring 56 is releasably restrained in a locking notch or socket 78 so as to secure the spring 56 in a tensioned mode. The notch 78 is formed in an upper zone of the rear wall 24 of the housing and opens downwardly to communicate with the horizontally extending guide slot 36 so that, upon downward displacement of the locking arm 74 and dislodgement of the arm 74 from the notch or socket 78, the pretensioned spring 56 is released so that the upper end section 66 of the spring 56 traverses an arcuate path across the width of the housing 22 with the arm 74 of the spring riding in the slot 36 and bearing against a downwardly presented edge 80 of the rear wall 24 of the housing 22 bounding a laterally-extending upper limit of the slot 36.

In the specific embodiment of the invention illustrated, the edge 80 is formed to include a section 84 executing an arcuate path vaulted upwardly. An adjacent, substantially horizontally extending connected section 86 provides, with the arcuate section 84, a cam surface defining a guide path for regulating movement of the spring arm 74 upon its release from restraint. That is, upon release of the spring 56 from its pretensioned mode, the spring arm 74 will bear against and travel along the wall edge 80 as the probe end 62 of the spring 56 pulses out through the aperture 60 and then automatically retracts to recede into the housing 22. In the illustrated embodiment, these surfaces 84 and 86 are also partially formed on an adjacent undersurface of the trigger bar 46.

As shown in FIGS. 2 through 5, the front wall 24 of the housing 22 is formed with a pair of generally parallel, laterally-spaced, vertically directed ribs 88 and 90 which diverge slightly in an upward direction and which are integrally formed with and extend along the front wall 24 and inwardly thereof, within the cavity 42 of the housing 22. The ribs 88 and 90 are aligned at lower ends thereof with corresponding lower end wall sections 94 and 96 of the housing 22, establishing the ribs as upwardly projecting, in-line extensions of the wall sections 94 and 96. This internal structure within the housing 22 delineates a vertically-extending guide channel 100 in which the looped section 70 of the spring 56 is restricted reciprocally to ride during execution of its functional movement when released from its initial, pre-tensioned mode.

Referring further to FIG. 2, the spring lancet 56 is shown in its initial pre-tensioned mode, the locking arm 74 being seated in the notch 78 and secured in place to immobilize the spring 56. The spring actuating bar 46 is shown in a housing-closing attitude, but not in a fully depressed position. The bar 46 carries on its undersurface a downwardly projecting elongate wall-like flange 104 (FIG. 6) which functions as a guide for an upper portion 108 of the spring section 66 of the spring 56 thereagainst when the bar 46 is fully depressed to release the spring 56. The upper section 66 of the spring 56 then moves rapidly across the width of the housing 22, interiorly thereof.

It will be understood that the spring 56 is released from its secured, tensioned mode by dislodging the arm 74 of the spring 56 from the locking notch 78. In the embodiment of the invention shown, this dislodgement is effected by application of digital pressure downwardly on the free end 110 of the bar 46 to bring an under-shoulder 112 of the actuating bar 46 to bear downwardly upon the arm 74 of the spring 56 and forcibly to displace the arm 74 from its seat in the locking notch 78. FIG. 2 shows the actuator bar 46 in a housing-closing mode, but in a standby position, and the spring 56 restrained and under tension, with the holding arm 74 locked in the notch 78.

Figure 3:
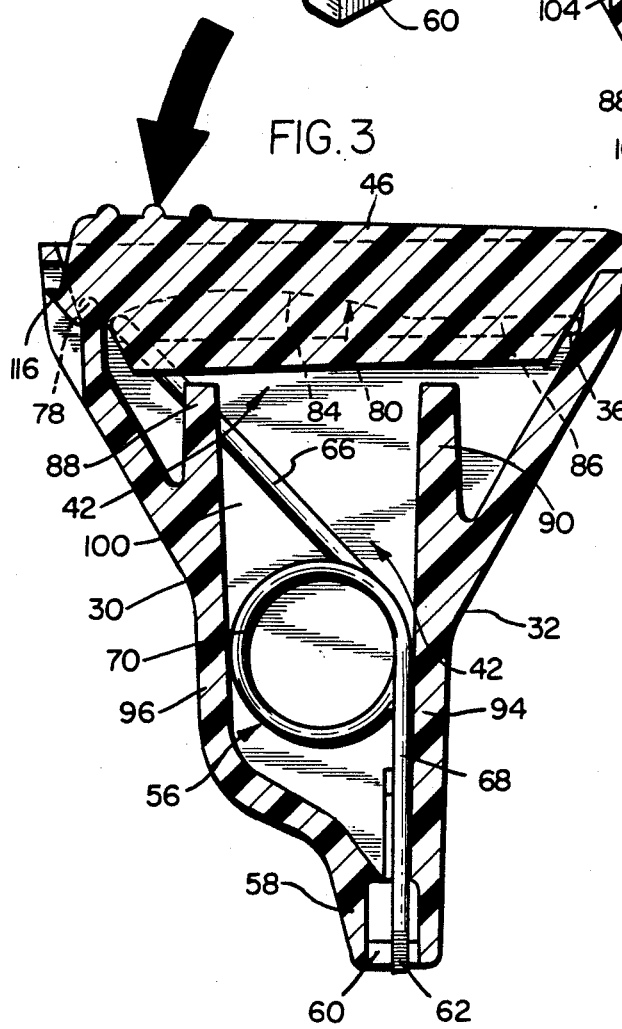
FIG. 3 is a cross-sectional view similar to that shown in FIG. 2 but with a lancet triggering arm displaced downwardly to dislodge the lancet from a restrained and tensioned mode and indicating an initial stage of travel of the probe end of the lancet outwardly through an aperture in the housing.

FIG. 3 depicts the spring 56 at the instant of dislodgement of the spring locking arm 74 from the retaining notch 78, the arm 46 having been urged downwardly and having dislodged the holding arm 74, thereby initiating the skin-piercing cycle. A wedge-like projection 116 on a forward end face of the bar 46 keys in cooperating opening 118 formed adjacent the top of the opposed side wall 26 to latch the bar 46 in a cavity-closing disposition in which the bar overlies the spring arm 74. The arrangement described permits digitally effected downward displacement of the bar 46 to dislodge and release the spring arm 74.

Referring also to FIG. 4, there is indicated schematically in FIG. 4 the orientation of the automatically retractable spring lancet 56 shortly after release of the locking arm 74. In FIG. 4, the spring section 66, being under tension from an initial distortion of the looped section 70, begins its swing laterally across the housing 22 with the arm riding along the camming guide edge 84. During this movement of the upper section 66 of the spring 56, and as shown in FIG. 4, the upper spring arm 66 assumes a transitory position in-line with the lower spring arm 68, the result being to establish a lengthened effective vertical expanse and reach of the spring 56 as the looped central section 70 and the lower section 68 of the spring 56 are urged downwardly in the guide channel 100. At the same instant, the sharpened probe end 62 of the lancet 56 is momentarily and forcibly advanced through the base aperture 60 in a manner to pierce the skin, should the lancet assembly be then supported in place, for example on the finger of a patient.

FIG. 4 illustrates an intermediate, transitory position and configuration of the spring section 66 when the probe end 62 of the lancet 56 extends at a maximum piercing travel distance through the orifice 60 and outwardly of the housing 22.

The continuing and uninterrupted steps in the travel sequence of the lancet spring 56 as it completes its reciprocal, probe-advancing and retracting cycle are shown in FIG. 5. As the upper section 66 of the spring lancet 56 continues its lateral travel beyond the point (FIG. 4) at which the upper section 66 is an in-line extension of the lower spring section 68, the over-all effective length of the spring 56 is foreshortened. When the spring 56 finally assumes a neutral end position and configuration in which the upper spring arm 66 abuts an upper angled portion 122 of the side wall 32 of the housing 22, as depicted in FIG. 5, the looped or coiled central section 70 is elevated within the channel 100 and, simultaneously, the probe end 62 is irreversibly and irretrievably retracted into and sequestered within the interior of the housing 22. The end 74 is visible through a top end opening 114 in the wall 34.

In assembling the automatically retractable lancet device of the invention, the spring 56, in its at-rest, untensioned configuration, is inserted into the housing 22 through the top opening 38, the closure bar 46 being hingedly pivoted to an open position as indicated in broken lines in FIG. 4. The lancet spring 56 assumes generally the position shown in FIG. 5.

To cock the spring 56 and set it at a tensioned mode, a machine finger or other suitable tool (not shown) is introduced into the housing 22 through the top opening to engage the spring section 66 adjacent the arm 74 and to displace the upper part 66 of the spring 56 laterally against its biasing force, thereby to seat the locking arm 74 in the spring-restraining locking socket 78. The closure bar 46 is then pivoted to assume the position indicated in FIGS. 1 and 2.

Alternatively, the bar 46 may be pivoted to a housing closing position immediately after insertion of the spring lancet 56. A machine finger may then be inserted into the horizontal slot 36 and moved laterally to pull back and cock the spring 56, locking the spring arm 74 in the retaining notch 78.

The device may conveniently be sterilized, after assembly, through the use of a sterilizing gas such as ethylene oxide Any other suitable sterilization technique may be employed.

While the structure of the automatically retractable lancet of the invention has been described with reference to certain structual materials, this fact should not be construed as limiting the invention in any sense. For example, the housing 22 may be molded from any preferred plastic, for example polypropylene or a copolymer of acrylonitrile, butadiene and styrene (ABS). The lancet spring is conveniently fabricated from stainless steel wire. The openings 36 and 114 in the housing are useful to show the location of the wire spring so that one may readily discern whether the unit has or has not been used.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limnited by the particular embodiment and specific construction described herein but should be definded by the appended claims and equivalents thereof. Accordingly, the aim in the appended claims is to cover all such changes and modifications as fall within the true spirit and scope of the invention.

The invention is claimed as follows:

1. A single-use, discardable lancet assembly including a lancet having a skin-puncturing probe and a housing in which said lancet is mounted and confined, said housing having front and rear walls and side walls connected thereto and extending therebetween, said housing being formed with a through aperture in an end thereof for movement of a probe therethrough for piercing the skin, said skin-producing probe of said lancet being mounted within and reciprocably movable in said housing, said probe having a sharpened point for puncturing the skin upon being forcibly urged thereagainst, a releasably-restrained, pretensioned torsion spring means integral with said probe and operable upon release of restraint for driving said sharpened point of said probe through a travel sequence initiated from a stand-by, retracted, restrained, and inoperative position of said probe and continuing through a functional disposition of said probe in which said point of said probe forcibly pulses downwardly to project through said aperture and outwardly of said housing and then immediately returns to a final, retracted and sequestered state in which said point resides irretrievably interiorly of said housing, spring securement means in said housing for restrictingly securing, confining, and restraining said spring means in a tensioned, biased configuration and for establishing said retracted, stand-by position of said reciprocably movable probe of said lancet in said housing, and spring guide means in said housing for delineating a path of movement of said spring means upon release thereof, non-resettably trigger means for releasing said spring from said spring securement means for initiating said spring means travel sequence, and means securing said trigger means to said housing for access exteriorly thereof and wherein said spring means comprises an elongated wire disposed to extend longitudinally in said housing, said wire having opposed upwardly and downwardly directed lineal end portions joined to an integrally formed intermediately-positioned looped section, said sharpened point being formed on an end of said downwardly directed end portion, wherein movement of said spring means within said housing and transition of said spring means between initial and final states is effective temporarily to vary an overall operational length dimension of said spring and reciprocally to extend and to retract relative to said housing end aperture, said downwardly directed end portion of said spring means including said sharpened point of said probe.

2. The structure as set forth in claim 1 wherein said spring guide means comprises an elongated through slot formed in one of said walls of said housing adjacent an upper zone thereof, said through slot extending generally laterally thereacross for guiding therewithin travel of said upwardly directed end portion of said spring means across said one of said walls.

3. The structure as set forth in claim 2, wherein said spring securement means comprises a spring-locking notch, said elongate slot communicating adjacent one lateral end thereof with said spring-locking notch, said notch being configured and located for engagement of said spring means therein and for lockingly restraining said spring means when said spring means is in said standby position and said upwardly directed lineal end portion of said wire having a terminal end section which forms a transversely projecting arm directed normally of said end portion of said wire for extending into and seating in said notch when said spring is in said standby position, and to ride along a lateral expanse of said slot upon actuation of said trigger means for forceably displacing said arm of said spring from said notch.

4. The structure as set forth in claim 3 wherein an upper wall edge bounding said slot includes an upwardly vaulted, arched sector delineating an arcuate camming edge defining a guide path to be traversed by said arm of said spring means upon release thereof from said notch.

5. The structure as set forth in claim 3 wherein said housing is formed with an access opening at the top, and wherein said trigger means includes a lever-like bar means for closing said opening in said housing and for actuating said spring means, flexible web means bridging between and hingedly joining an upper end edge of said bar means to an upper terminus of a sidewall of said housing, said bar means being digitally manipulatable about said web means and positionable to overlie and matingly to seat in the top opening of said housing as a closure therefor, and wherein said trigger means includes shoulder means integrally formed with said bar means for mechanically engaging said arm of said spring means restrained in said notch and for displacing said arm to release said spring means from said standby position and to activate said spring means upon pivotal manipulation of said bar means during forced downward displacement thereof into said opening of said housing.

6. The structure as set forth in claim 5 wherein said shoulder means for mechanically engaging said spring means comprises a downwardly directed abutment surface for engaging said arm of said spring means for urging said arm downwardly to displace said arm from said spring-locking notch.

7. The structure as set forth in claim 5 wherein said flexible web means is integrally formed with said bar means and said housing.

8. The structure as set forth in claim 5 wherein an undersurface of said bar means defines an upper slot and includes an upwardly vaulted, arched sector delineating an arcuate camming edge defining a guide path to be traversed by said arm of said spring means upon release thereof from said notch.

9. The structure as set forth in claim 1 wherein said spring guide means further includes a pair of generally vertically-directed, laterally-spaced ribs in said housing and extending from and along one of said front and rear walls interiorly thereof, said ribs being spaced to define a vertical guide channel delineating a path for reciprocal movement of said looped section of said spring means therewithin during functional operation of said spring means.

* * * * *